United States Patent [19]

Gephart

[11] Patent Number: 4,557,604
[45] Date of Patent: Dec. 10, 1985

[54] FLOPPY DISK TRANSMISSIVITY METER

[75] Inventor: Russell L. Gephart, Fremont, Calif.

[73] Assignee: Verbatim Corporation, Sunnyvale, Calif.

[21] Appl. No.: 107,177

[22] Filed: Dec. 26, 1979

[51] Int. Cl.$^4$ ............................................. G01N 21/00
[52] U.S. Cl. .................................. 356/432; 356/443; 250/562
[58] Field of Search ............... 356/432, 443, 444, 436, 356/440, 441, 447, 237, 239; 250/562, 563, 542

[56] References Cited

U.S. PATENT DOCUMENTS

| | | | |
|---|---|---|---|
| 2,500,547 | 3/1950 | Kalmus et al. | 356/432 |
| 3,430,054 | 2/1969 | Klein | 250/552 |
| 3,711,210 | 1/1973 | Krukonski | 356/438 |
| 3,807,875 | 4/1974 | Fischer et al. | 356/432 |
| 3,832,065 | 8/1974 | Sullivan et al. | 356/447 |
| 3,942,898 | 3/1976 | Anderson | 356/443 |

Primary Examiner—R. A. Rosenberger
Attorney, Agent, or Firm—Thomas E. Schatzel

[57] ABSTRACT

A meter for measuring the transmissivity of a floppy disk including an oscillator for generating a sinusoidal signal, a driver and an LED, biased on by the driver and modulated by the driver responsive to the sinusoidal signal, the LED for illuminating a portion of a surface of the disk. The meter further including a photodetector optically aligned with the LED and so disposed as to develop a detected signal from illumination transmitted through the disk, a current to voltage converter, an amplifier, a state variable band pass filter, and a peak detector and amplifier for amplifying, filtering and detecting the detected signal to develop a signal suitable for driving a digital panel meter so as to directly indicate in percent the transmissivity of the disk.

19 Claims, 1 Drawing Figure

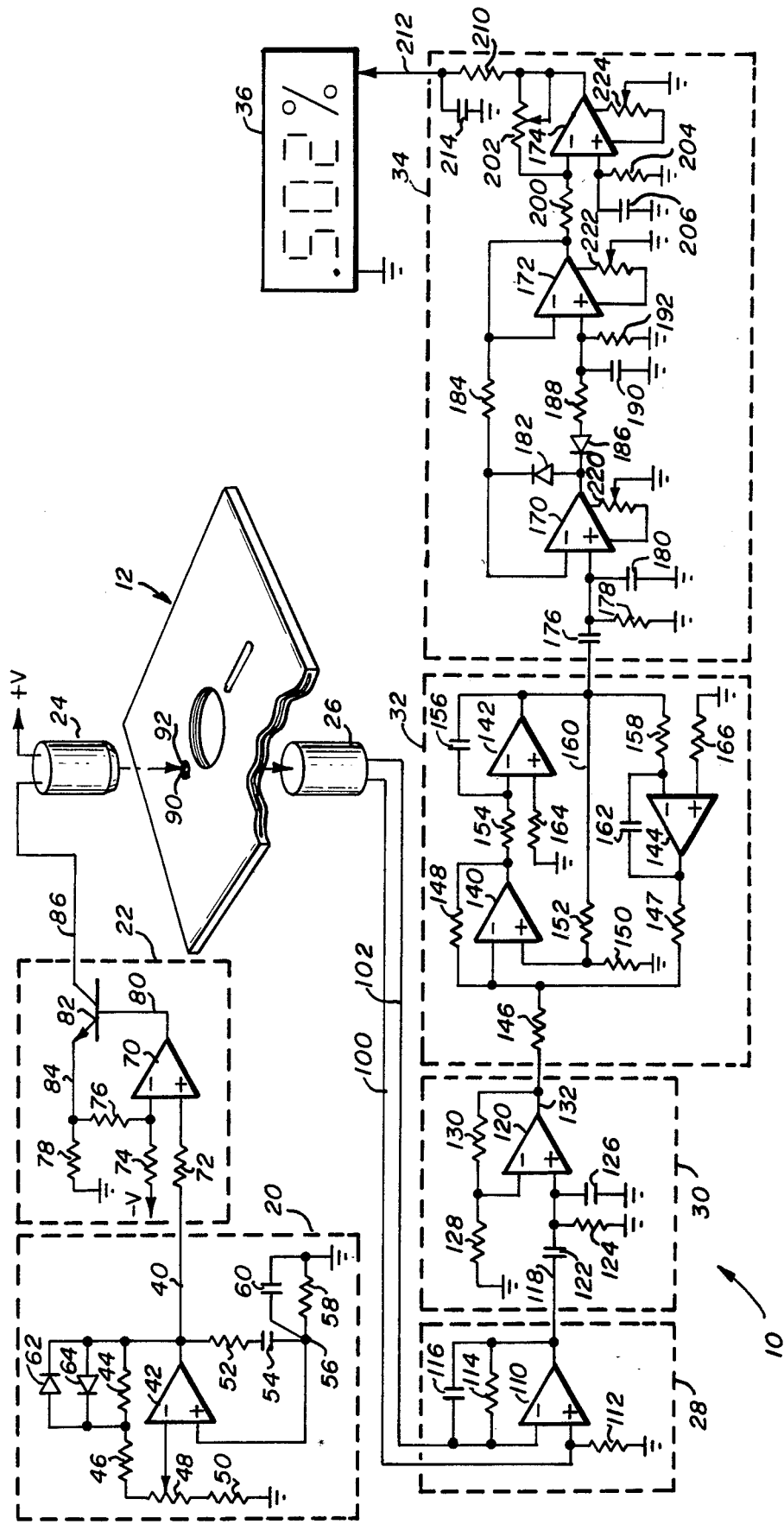
Fig_1

FLOPPY DISK TRANSMISSIVITY METER

BACKGROUND OF THE INVENTION

1. Field of the Invention

The present invention relates generally to meters and more specifically to a meter for making accurate and precise measurements of the transmissivity of floppy disks to radiation in the infrared spectrum.

2. Description of the Prior Art

An important vehicle for information storage is the floppy disk also referred to as a flexible disk or diskette. As the name implies, a floppy disk is a thin round piece of flexible magnetic recording material, such as heavy oxide coated mylar based magnetic tape recording material. The floppy disk contains a large centrally located spindle hole and a small index hole, a common location for which is near the spindle hole. Additionally, some floppy disks, called hard sectored disks, each contain a plurality of small sector holes located at equal angular increments around the disk at the same radius as the sector hole. Further, floppy disks are manufactured in a variety of sizes including a size which resembles a 45 RPM record, referred to as 8 inch, and a smaller size, referred to as 5¼ inch or simply 5 inch.

Many floppy disks are enclosed, each between a pair of soft, low friction, anti-static liners within a square shaped protective envelope, also commonly referred to as a cartridge or jacket. Each such envelope contains a number of openings which are aligned on opposite sides of the envelope and open through the liners to provide access to the floppy disk. A pair of large round centrally located openings permit the edge of the floppy disk around the spindle hole to be engaged between a hub and a motor driven spindle to rotate the disk within its envelope. A pair of radially aligned slotted openings permit a pair of opposed read/write heads, or a head and a pressure pad, to access opposite surfaces of the floppy disk along a radial line over the extent of the information storage area. Further, a pair of small openings are located at the same radius as the index and sector holes.

The area of the floppy disk upon which information is recorded is divided into a plurality of imaginary concentric rings called tracks. Each of the tracks is divided into a plurality of equal angular portions called sectors. Sector synchronization is provided by the index hole. On floppy disks which lack sector holes, called soft sectored disks, sector delineation and identification is provided by information recorded directly on each of the tracks. Sector holes, on hard sectored disks, provide this function. Each sector hole delineates a sector which is identified by counting the number of sector holes from the index hole.

Detection of the index hole and, on hard sectored floppy disks, the sector holes is provided by a sensor that includes the combination of a light emitting diode (LED) and a photodetector. The LED is disposed on one side of the floppy disk aligned with the index hole opening in the disk envelope so as to illuminate the disk therethrough. The photodetector is disposed on the opposite side of the floppy disk optically aligned with the LED so as to detect illumination passing through the index hole or each of the sector holes when one is rotated into alignment with the optical path.

Unfortunately, the index hole sensor is highly susceptible to false triggering caused by LED generated illumination being transmitted through the floppy disk. To minimize such problems standards are being developed for the maximum acceptable floppy disk transmissivity, i.e. the ratio of the energy transmitted through the disk to that which is incident thereon.

A proposed standard promulgated by the American National Standards Institute in a publication known as "The Twelfth Draft of the American National Standard for Single Sided Unformatted Flexible Disk Cartridges" establishes a maximum floppy disk transmissivity to infrared radiation of 900 nanometers wave length of ½% where the maximum transmissivity is defined by a reading obtained with a neutral density filter of known transmissivity between 0.45% and 0.55% calibrated with 900 nanometer radiation. Obviously, both the accuracy and the precision with which the transmissivity of a floppy disk may be measured is of considerable moment. It is important to insure that floppy disks meet this proposed standard without rejecting good disks or imposing unnecessarily stringent manufacturing requirements.

Relevant to the problems of measuring transmissivity are a number of prior art disclosures. Henry P. Kalmus et al in U.S. Pat. No. 2,500,547 review the use of a rotating shutter to modulate a light source used in transmissivity or reflectivity measurements to permit the detected transmitted or reflected energy to be amplified by an AC amplifier rather than a relatively unstable DC tube amplifier. Further, Kalmus et al disclose a densitometer which includes a multi-vibrator or thyratron oscillator used to modulate a lamp to a depth of approximately 100% and a tuned amplifier to amplify the output of a photo-sensitive element to develop a meter driving signal.

A densitometer for chemical analysis is disclosed in U.S. Pat. No. 3,807,875 by David J. Fischer et al. The disclosed densitometer includes a mono-stable multivibrator for developing pulses which are used to drive a gallium arsenide LED to develop radiation at a wave length of approximately 0.9 microns for illuminating materials to be measured. Also included are a semiconductor phototransistor for detecting LED radiation attenuated by the sample, an amplifier for amplifying the detected signal, and a peak detector and hold circuit gated responsive to each of the pulses of the mono-stable multivibrator to generate a meter driving signal that is proportional to the peak of the amplified detected signal. Although indicating that noise is a problem in making high absorption measurements, Fischer et al indicate that they avoid the problem by only making relative, rather than absolute, measurements.

To provide an alternative to the use of a flashlight in detecting hydrocephalus, Curtis C. Johnson discloses in U.S. Pat. No. 3,674,008 an apparatus for measuring the optical density of a human skull. The disclosed apparatus includes a triggering pulse generating oscillator and a strobe or flashlamp controlled thereby for illuminating a portion of a skull. Resultant illumination at another portion of the skull is detected by a photo-multiplier, filtered and stored in a sample-and-hold circuit responsive to the oscillator, to develop a display driving signal. It is suggested that the strobe and photo-multiplier may be replaced by a gallium arsenide diode and a silicon photo-detecting diode, respectively.

A meter for measuring the opacity of smoke discharged in the exhaust of a motor vehicle is disclosed by Richard Krukowski in U.S. Pat. No. 3,711,210. The disclosed meter employs a pulse generator driven gallium phosphide device for developing light pulses. A combination of a silicon phototransistor, a band pass filter tuned to the frequency of the light pulses, an amplifier, a detector and a hold circuit are employed to develop a meter driving signal that is proportional to the opacity of smoke between the gallium phosphide device and the photo-transistor. A tungsten biasing lamp and associated circuitry are also employed to maintain a constant voltage offset at the output of a photo-transistor to compensate for variations in ambient light.

Smoke detectors employing multi-vibrator driven light sources are disclosed in the U.S. Pat. No. 3,524,707 issued to Julian E. Hansen et al and U.S. Pat. No. 3,846,772 issued to William T. Peberdy. The Hansen disclosure employs a band pass filter in the light receiver circuitry. The Peberdy disclosure employs a gallium arsenide diode, emitting infrared radiation and an amplifier in the radiation detecting circuitry which is tuned to those frequencies that are produced by hot gases.

Also of interest is the apparatus for measuring drops or globules of liquid, such as oil, dispersed in another liquid, such as water, disclosed by Norman A. Lyshkow in U.S. Pat. No. 3,864,044 and the nephelometer disclosed by William B. Underwood in U.S. Pat. No. 4,118,625.

Although the above-mentioned references are of interest, the need to make accurate and precise measurements of the transmissivity of a floppy disk at an infrared wave length to insure compliance with disk standards presents unique problems not addressed by these references.

SUMMARY OF THE PRESENT INVENTION

It is therefore an object of the present invention to provide a means for measuring the transmissivity of a floppy disk so as to assure compliance with applicable standards.

Another object of the present invention is to provide a means for measuring to a precision of at least 0.01% the transmissivity of a floppy disk to radiation having a wave length of approximately 900 nanometers.

Briefly, the preferred embodiment of the present invention includes an oscillator for generating a sinusoidal signal, a driver for developing from the sinusoidal signal a biasing signal modulated by the sinusoidal signal and an LED disposed on one side of a floppy disk and driven by the driver so as to illuminate a portion of the surface of the disk. Also included is a photo-detector disposed on the other side of the floppy disk and optically aligned with the LED so as to develop a detected signal from illumination transmitted by the disk, an amplifier for developing an amplified detected signal, a state variable filter operated as a band pass filter tuned to the oscillator frequency for developing a filtered signal from the amplified detected signal and a peak detector and amplifier for developing from the filtered detected signal a signal suitable for driving a digital panel meter so as to indicate in percent the transmissivity of the floppy disk.

Thus, the ability to ascertain the compliance of a floppy disk with applicable transmissivity standards is a material advantage of the present invention.

Another advantage of the present invention is the ability to measure to an accuracy of ±0.003% the transmissivity of a floppy disk to radiation of a wave length of 900 nanometers in 0.001% increments.

These and other objects and advantages of the present invention will no doubt become apparent to those of ordinary skill in the art after having read the following detailed description of the preferred embodiment illustrated in the drawing figure.

IN THE DRAWING

FIG. 1 is a combined perspective view and schematic diagram of a floppy disk transmissivity meter in accordance with the present invention.

DETAILED DESCRIPTION OF THE PREFERRED EMBODIMENT

Illustrated in FIG. 1 in combined perspective view and schematic diagram form and generally designated by the number 10 is a meter in accordance with the present invention for measuring the transmissivity of a floppy disk such as that which is generally designated by the number 12. Meter 10 includes a Wien bridge oscillator 20, a light emitting diode (LED) driver 22, an LED 24, a photodetector 26, a current-to-voltage converter 28, a preamplifier 30, a state variable filter 32, a peak detector and amplifier 34 and a digital panel meter 36.

Oscillator 20 is of the Wien bridge type for developing a sinusoidal signal on a line 40. The use of a sinusoidal signal is important to prevent phase distortion from affecting the accuracy of the meter. The principal components of oscillator 20 include a Wien bridge and an operational amplifier 42. One leg of the bridge, formed by a resistor 44, a resistor 46, a potentiometer 48 and a resistor 50 all connected in series between line 40 and circuit ground, provides negative feedback for the oscillator. Positive feedback is provided by the other leg of the bridge, formed by a resistor 52 and a capacitor 54 connected in series between line 40 and a node 56 and a resistor 58 and a capacitor 60 connected in parallel between node 56 and circuit ground. A pair of oscillator stabilizing diodes 62 and 64 are connected back-to-back across resistor 44. Operational amplifier 42 has an inverting input connected to the wiper of potentiometer 48, a non-inverting input connected to node 56 and an output connect to line 40.

In the preferred embodiment, the impedance of resistors 52 and 58 and capacitors 54 and 60 is such that oscillator 20 operates at a frequency of approximately 2 kilohertz, a frequency chosen to minimize both power line noise and high frequency circuit limitations. Additionally, the impedance of the resistive elements 52 and 58 is similar, as is that of the capacitive elements 54 and 60, providing a positive feedback of one third, somewhat more than the negative feedback provided by resistors 44, 46 and 50 and potentiometer 48 until the conduction of diodes 62 and 64. Thus, the level of the oscillation is controlled by potentiometer 48, which, in the preferred embodiment, is adjusted such that a 4 volt peak-to-peak sinusoidal signal is developed on line 40.

Driver 22 includes an operational amplifier 70 having a non-inverting input coupled by an offset cancelling resistor 72 to line 40, an inverting input coupled to a negative power supply potential by a summing resistor 74 and to circuit ground by the series combination of a summing resistor 76 and a current sensing resistor 78. Additionally, amplifier 20 has an output connected by a line 80 to the base of an NPN transistor 82, the emitter of which is connected by a line 84 to the juncture of resistors 76 and 78. The collector of transistor 82 is coupled by a line 86 and LED 24 to a positive power supply potential.

Preferably, the impedance of resistor 78 is such that a potential of 1 volt is developed on line 84 when 10 milliamps of current flows through LED 24. The impedance of resistors 74 and 76 is such that LED 24 is biased with a current flow of 30 milliamps when 0 volts is developed on line 40, a bias chosen to correspond to the most linear region of LED 24. To minimize the effects of current flow at the input of amplifier 70, the impedance of resistor 72 is made similar to that measured at the inverting input of amplifier 70, the parallel combination of the impedance of resistor 74, with the sum of the impedances of resistors 76 and 78.

In the preferred embodiment, LED 24 is of the type which is designated MLED 930 by the Motorola Corporation. LED 24 is so disposed, with respect to a floppy disk the transmissivity of which is to be measured, as to illuminate the surface of the disk through an index hole opening in the envelope thereof, such as an opening 90 and a surface 92 of floppy disk 12.

Photo-detector 26, which is preferably of the type which is designated OCLI 44PDO5M by the Optical Coating Laboratory, Inc., is optically aligned with LED 24 so as to develop, between a pair of lines 100 and 102, a current flow that is proportional to the illumination transmitted by the floppy disk.

Current-to-voltage converter 28 provides a low impedance load to photo-detector 26. Converter 28 includes an operational amplifier 110 having a non-inverting input connected to line 100 and coupled to circuit ground by an offset cancelling resistor 112, an inverting input and an output. The inverting input of amplifier 110 is connected to line 102 and coupled by the parallel combination of a feedback resistor 114 and a roll-off capacitor 116 to the output of the amplifier which is connected to a line 118.

Resistors 112 and 114 establish the conversion efficiency of converter 28, preferably, at 0.1 volts per microamp. The impedance of resistor 112 is similar to that of resistor 114 so as to minimize temperature effects. Resistor 112 also establishes a reference potential at the non-inverting input of amplifier 110. Capacitor 116 provides a high-frequency roll-off of the conversion efficiency of converter 28 both to attenuate high frequency noise and to stabilize the converter.

Preamplifier 30 includes an operational amplifier 120 having a non-inverting input, an inverting input and an output. The inverting input of amplifier 120 is coupled by a DC blocking capacitor 122 to line 118 and by the parallel combination of an offset cancelling resistor 124 and a noise filtering capacitor 126 to circuit ground. The inverting input of amplifier 120 is coupled by a first gain determining resistor 128 to circuit ground and by a second gain determining resistor 130 to the amplifier output which is connected to a line 132.

Preferably, the impedance of resistors 128 and 130 is such that preamplifier 30 has a voltage gain of approximately 11. Resistor 124, like resistor 112 both minimizes temperature effects and establishes a biasing potential, in this case at the non-inverting input of amplifier 120.

Filter 32 is of the type which is commonly referred to as a state space filter, state variable active filter or a universal filter. In the present invention, filter 32 is operated as a second order band pass filter. Filter 32 includes a summing stage employing an operational amplifier 140, two integrating stages each employing one of a pair of operational amplifiers 142 and 144, and a Q determining feedback network. All three amplifiers 140, 142 and 144 each have a non-inverting input, an inverting input and an output. The inverting input of amplifier 140 is coupled to line 132 by a summing resistor 146, to the output of amplifier 144 by a summing resistor 147 and to the output of amplifier 140 by a feedback resistor 148.

The inverting input of amplifier 140 is coupled to circuit ground by one of the Q determining resistors, a resistor 150, and by the other Q determining resistor, a resistor 152, to the output of amplifier 142. The inverting input of amplifier 142 is coupled by a summing resistor 154 to the output of amplifier 140 and by an integrating capacitor 156 to the output of amplifier 142. Similarly, the inverting input of amplifier 144 is coupled by a summing resistor 158 to the output of amplifier 142 which is connected to a line 160 and by an integrating capacitor 162 to the output of amplifier 144. Additionally, the non-inverting inputs of amplifiers 142 and 144 are coupled to circuit ground each by an offset cancelling resistor, a resistor 164 and a resistor 166, respectively.

Since the impedance of capacitors 156 and 162 and the impedance of resistors 154 and 158 determine the center frequency of the filter, resistors 154 and 158 are chosen to have an impedance similar to that of resistor 52 and capacitors 156 and 162 are chosen to have an impedance similar to that of capacitor 54 such that the center frequency of the filter is aligned with the oscillation frequency of oscillator 20. Preferably, the impedance of resistor 152 is approximately 20 times greater than that of resistor 150 to establish the Q of filter 32 at a moderate value. Finally, for minimum offset, resistors 164 and 166 are chosen to have an impedance similar to that of resistors 154 and 158.

In an alternative embodiment, an equivalent configuration of filter 32 is employed, one in which resistor 146 is connected between the inverting input of amplifier 140 and circuit ground and resistor 150 is connected between the non-inverting input of amplifier 140 and the output of amplifier 120.

Peak detector and amplifier 34 include three operational amplifiers 170, 172 and 174 each having a non-inverting input, an inverting input, and an output. The non-inverting input of amplifier 170 is coupled by a DC blocking capacitor 176 to line 160, and to circuit ground by the parallel combination of an offset cancelling resistor 178 and a noise filtering capacitor 180. The inverting input of amplifier 170 is coupled to the output thereof by a positive swing limiting diode 182 and to the inverting input of amplifier 172 and the output thereof by an isolating resistor 184.

The output of amplifier 170 is coupled to the non-inverting input of amplifier 172 by the series combination of a steering, or isolating, diode 186 and a resistor 188, the latter for determining the attack time of the peak detector. Coupling the non-inverting input of amplifier 172 to circuit ground is the parallel combination of a peak holding capacitor 190 and a resistor 192, the latter for determining the decay time of the peak detector.

The inverting input of amplifier 174 is coupled to the output of amplifier 172 by a summing resistor 200 and connected to one end of a meter calibrating feedback potentiometer 202, the other end and wiper of which are connected to the output of amplifier 174. The non-inverting input of amplifier 174 is coupled to circuit ground both by an offset cancelling resistor 204 and a noise filtering capacitor 206. A filtering resistor 210 is connected between the output of amplifier 174 and a line which is coupled to circuit ground by a filter capacitor 214. Line 212 is also coupled to circuit ground by digital panel meter 36.

Additionally, amplifiers 170, 172 and 174 each have a pair of inputs which are connected to ends of a respective one of three offset adjusting potentiometers 220, 222 and 224, all of which have wipers that are connected to circuit ground.

In the preferred embodiment, the time constant determined by resistor 188 and capacitor 190 and that determined by resistor 192 and capacitor 190 are of the order of 0.001 seconds and 0.1 seconds, respectively. Also, preferably, amplifiers 42, 70, 120, 140, 142 and 144 are of the type which are commonly designated in the art LM741, and amplifiers 110, 170, 172 and 174 are of the type which are commonly designated in the art LF351.

Digital panel meter 36 is preferably a 3½ digit, 2 volt full-scale, digital panel meter such as that which is designated DM-4100N by the Datel Corporation. As such, meter 36 directly displays, in 0.001 increments, the transmissivity of a floppy disk which is being measured. It has been found that the displayed transmissivity is accurate to within ±0.003%.

It is contemplated that after having read the preceding disclosure certain alterations and modifications of the present invention will no doubt become apparent to those skilled in the art. It is therefore intended that the following claims be interpreted to include all such alterations and modifications as fall within the true spirit and scope of the invention.

What is claimed is:

1. A meter for measuring the transmissivity of a floppy disk, the meter comprising in combination:
   an oscillator for generating a sinusoidal signal;
   a driver coupled to said oscillator for developing a modulated biasing signal from said sinusoidal signal;
   an LED coupled to said driver for generating a sinusoidally modulated beam of infrared radiation from said modulated biasing signal, said LED being so disposed with respect to the floppy disk as to illuminate at least a portion of the surface thereof;
   a photodetector suitably disposed with respect to said floppy disk so as to intercept at least a portion of the LED generated radiation that is transmitted through said floppy disk, said photodetector for generating a radiation detected signal from said intercepted radiation;
   coupling means;
   a state space type bandpass filter coupled to said photodetector by said coupling means, said filter for developing a filtered signal from those components of said radiation detected signal that have a frequency substantially that of said sinusoidal signal;
   detector means coupled to said filter, said detector means for developing a detected filtered signal from the peak excursions of said filtered signal; and
   display means coupled to said detector means, said display means for indicating the level of said detected filtered signal, whereby the transmissivity of said floppy disk may be ascertained.

2. A meter as recited in claim 1 wherein said oscillator is of the Wien bridge configuration.

3. A meter as recited in claim 1 wherein said oscillator includes a source of reference potential; an operational amplifier having an inverting input, a non-inverting input and an output; a first resistor; a first capacitor having a first end coupled by said first resistor to said output and a second end connected to said non-inverting input; a second resistor connected between said non-inverting input and said reference potential; a second capacitor connected between said non-inverting input and said reference potential; first resistive means connected between said output and said inverting input; and a second resistive means connected between said inverting input and said reference potential, whereby said sinusoidal signal is generated at said output.

4. A meter as recited in claim 3 wherein said first resistive means includes a third resistor; a fourth resistor having a first end coupled by said third resistor to said inverting input and a second end connected to said output; a first diode connected in parallel with said fourth resistor; and a second diode so connected in parallel with said fourth resistor as to be connected back-to-back with said first diode.

5. A meter as recited in claim 1 wherein said driver includes a first potential source; a second potential source; a third potential source; a first resistor; a second resistor; a third resistor; an operational amplifier having a non-inverting input coupled to said oscillator for receiving said sinusoidal signal, an inverting input coupled by said first resistor to said first potential source and an output; and a transistor having a base coupled to said output, an emitter coupled by said second resistor to said second potential source and coupled by said third resistor to said inverting input and a collector coupled by said LED to said third potential source.

6. A meter as recited in claim 1 wherein said LED is of the type which is designated MLED 930 by the Motorola Corporation.

7. A meter as recited in claim 1 wherein said photodetector is of the type which is designated OCLI 44PDO5M by the Optical Coating Laboratory, Inc.

8. A meter as recited in claim 1 wherein said coupling means includes a current-to-voltage converter having an input connected to said photodetector and an output coupled to said bandpass filter.

9. A meter as recited in claim 1 wherein said coupling means includes a first resistor; a second resistor; a capacitor; a reference potential; and an operational amplifier having a non-inverting input coupled by said first resistor to said reference potential, an inverting input coupled by said photodetector to said non-inverting input and an output coupled by said second resistor to said inverting input, coupled by said capacitor to said inverting input and coupled to said bandpass filter.

10. A meter as recited in claim 9 wherein said operational amplifier is of the type which is commonly designated in the art LF 351.

11. A meter as recited in claim 1 wherein said detector means includes a resistor; a capacitor; a diode; a reference potential; a first operational amplifier having a non-inverting input coupled to said bandpass filter, an inverting input and an output; and a second operational amplifier having a non-inverting input coupled by said resistor to said reference potential, by said capacitor to said reference potential and by said diode to said output of said first operational amplifier, an inverting input and an output coupled to said inverting input of said second operational amplifier, coupled to said inverting input of said first operational amplifier and coupled to said display means.

12. A meter as recited in claim 1 wherein said display means is a digital panel meter.

13. A meter as recited in claim 1 wherein said bandpass filter includes a source of reference potential; a first resistor having a first end and a second end; a second resistor having a first end and a second end; a third resistor; a fourth resistor; a fifth resistor; a sixth resistor; a seventh resistor; a first capacitor; a second capacitor; a first operational amplifier having an inverting input connected to said first end of said first resistor, a non-inverting input connected to said first end of said second resistor and an output coupled to said inverting input of said first operational amplifier by said third resistor; a second operational amplifier having an inverting input coupled by said fourth resistor to said output of said first operational amplifier and an output coupled by said first capacitor to said inverting input of said second operational amplifier, by said fifth resistor to said non-inverting input and to said detector means; and a third operational amplifier having an inverting input coupled by said sixth resistor to said output of said second operational amplifier and an output coupled by said second capacitor to said inverting input of said third operational amplifier and by said seventh resistor to said inverting input of said first operational amplifier, one of said second ends of said first and said second resistor being connected to said reference potential and the other of said second ends of said first and said second resistors being coupled by said coupling means to said photodetector.

14. A meter as recited in claim 13 wherein said oscillator is of the Wien bridge configuration.

15. A meter as recited in claim 13 wherein said oscillator includes a fourth operational amplifier having an inverting input, a non-inverting input and an output; an eighth resistor; a third capacitor having a first end coupled by said eighth resistor to said output of said fourth operational amplifier and a second end connected to said non-inverting input of said fourth operational amplifier; a ninth resistor connected between said non-inverting input of said fourth operational amplifier and said reference potential; a fourth capacitor connected between said non-inverting input of said fourth operational amplifier and said reference potential; first resistive means connected between said output and said inverting input of said fourth operational amplifier; and a second resistive means connected between said inverting input of said fourth operational amplifier and said reference potential, whereby said sinusoidal signal is generated at said output of said fourth operational amplifier.

16. A meter as recited in claim 15 wherein said LED is of the type which is designated MLED 930 by the Motorola Corporation.

17. A meter as recited in claim 15 wherein said photodetector is of the type which is designated OCLI 44PDO5M by the Optical Coating Laboratory, Inc.

18. A meter as recited in claim 15 wherein said coupling means includes a tenth resistor; an eleventh resistor; a fifth capacitor; and a fifth operational amplifier having a non-inverting input coupled by said tenth resistor to said reference potential, an inverting input coupled by said photodetector to said non-inverting input of said fifth operational amplifier and an output coupled by the parallel combination of said eleventh resistor and said fifth capacitor to said inverting input of said fifth operational amplifier and coupled to said bandpass filter.

19. A meter as rectied in claim 18 wherein said fifth operational amplifier is of the type which is commonly designated in the art LF 351.

* * * * *